US009320772B2

(12) United States Patent
Doron et al.

(10) Patent No.: US 9,320,772 B2
(45) Date of Patent: Apr. 26, 2016

(54) HERBAL COMPOSITION FOR TREATING ANXIETY RELATED CONDITIONS

(75) Inventors: Ravid Doron, Tel Aviv (IL); Nadav Kately, Raanana (IL)

(73) Assignee: OPMOP LTD., Raanana (IL)

( * ) Notice: Subject to any disclaimer, the term of this patent is extended or adjusted under 35 U.S.C. 154(b) by 134 days.

(21) Appl. No.: 13/583,481

(22) PCT Filed: Mar. 8, 2011

(86) PCT No.: PCT/IL2011/000221
§ 371 (c)(1),
(2), (4) Date: Dec. 3, 2012

(87) PCT Pub. No.: WO2011/111039
PCT Pub. Date: Sep. 15, 2011

(65) Prior Publication Data
US 2013/0149370 A1    Jun. 13, 2013

Related U.S. Application Data

(60) Provisional application No. 61/311,537, filed on Mar. 8, 2010.

(51) Int. Cl.
| A61K 47/00 | (2006.01) |
| A01N 65/00 | (2009.01) |
| A61K 36/899 | (2006.01) |
| A61K 36/725 | (2006.01) |
| A61K 36/734 | (2006.01) |
| A61K 36/8967 | (2006.01) |

(52) U.S. Cl.
CPC ............. *A61K 36/899* (2013.01); *A61K 36/725* (2013.01); *A61K 36/734* (2013.01); *A61K 36/8967* (2013.01)

(58) Field of Classification Search
USPC ................................................. 424/439, 750
See application file for complete search history.

(56) References Cited

U.S. PATENT DOCUMENTS

| 7,790,928 B1 * | 9/2010 | Hechinger ...................... 568/27 |
| 2004/0180104 A1 | 9/2004 | Lin |

FOREIGN PATENT DOCUMENTS

| CN | 101555448 A | 10/2009 |
| CN | 101607027 A | 12/2009 |

OTHER PUBLICATIONS

Fruehauf, "Commonly Used Chinese Herb Formulas For the Treatment of Mental Disorders," Journal of Chinese Medicine, vol. 48, Issue 48, pp. 21-34 (1995).*
Tsung-Yi Lin, "Neurasthenia Revisited: Its Place in Modern Psychiatry," Culture, Medicine and Psychiatry, vol. 13, Issue 2, pp. 105-129 (1989).*
Flaws et al, "Chinese Medical Psychiatry: A Textbook & Clinical Manual: Including Indications for Referral to Western Medical Services," Blue Poppy Enterprises, Inc., p. 271 (2001).*
Barbui C., Cipriani A., Review: maintenance antidepressants reduce risk of relapse but effect is not as great in recurrent depression, British Medical Journal, 2009, p. 79, vol. 12, No. 3, EBMH, United Kingdom.
Butterweck V., Hegger M., Winterhoff H., Flavonoids of St. John's Wort reduce HPA axis function in the rat. Planta Med, 2004, pp. 1008-1011, vol. 70, United States.
Chen Z.Y., Zhang Z.S., Kwan K.Y., Zhu M., Ho W.K., Huang Y., Endothelium-dependent relaxation induced by hawthorn extract in rat mesenteric artery, Life Sci., 1998, pp. 1983-1991, vol. 63, No. 22, Elsevier, United States.
Chouinard G., Issues in the clinical use of benzodiazepines: potency, withdrawal, and rebound, J Clin Psychiatry, 2004, pp. 7-12, vol. 65, Physicians Postgraduate Press, Inc., Unied States.
Corder R., Warburton R.C., Khan N.Q., Brown R.E., Wood E.G., Lees D.M., The procyanidin-induced pseudo laminar shear stress response: a new concept for the reversal of endothelial dysfunction, Clinical Science 2004, pp. 513-517, vol. 106, Great Britain.
Cui T., Nakamura K., Tian S., Kayahara H., Tian Y.L., Polyphenolic content and physiological activities of Chinese hawthorn extracts, Biosci Biotechnol Biochem, 2006, pp. 2948-2956, vol. 70, United States.
Davydov M, Krikorian AD, *Eleutherococcus senticosus* (Rupr. & Maxim.) Maxim. (Araliaceae) as an adaptogen: a closer look, Journal of Ethnopharmacology, 2000, pp. 345-393, vol. 72, Elsevier, Netherlands.
Dording C.M., Mischoulon D., Petersen T.J., Kornblum R., Gordon J., Nierenberg A.A., Rosenbaum J.F., Fava M., The pharmacologic management of SSRI-induced side effects: a survey of psychiatrists Annals of Clinical Psychiatry, 2002, pp. 143-147, vol. 14, No. 3, United States.
Ko K.M., Leung H.Y., Enhancement of ATP generation capacity, antioxidant activity and immunomodulatory activities by Chinese Yang and Yin tonifying herbs, Chinese Medicine, 2007, pp. 1-10 vol. 2, No. 3, BioMed Central, Great Britain.
Lin R.D., Hou W.C., Yen K.Y., Lee M.H., Inhibition of monoamine oxidase B (MAO-B) by Chinese herbal medicines, 2003, Phytomedicine, pp. 650-656, vol. 10, Urban & Fischer Verlag, Germany.
cEwen B.S., Protective and damaging effects of stress mediators. New England Journal of Medicine,1998, pp. 171-179, vol. 338, No. 3, Massachusetts Medical Society, United States.
Panossian A., Gabrielian E., Wagner H., On the mechanism of action of plant adaptogens with particular reference to cucurbitacin R diglucoside. Phytomedicine, 1999, pp. 147-155, vol. 6, No. 3, Urban & Fischer Verlag, Germany.
Pelissolo. A., Efficacy and tolerability of escitalopram in anxiety disorders: a review., Ecephale. 2008, pp. 400-408, vol. 34, Elsevier, Netherlands.

(Continued)

*Primary Examiner* — Dennis J Parad
(74) *Attorney, Agent, or Firm* — Browdy and Neimark, PLLC

(57) ABSTRACT

The present invention relates to herbal compositions for the treatment and/or prevention of anxiety disorders or stress. These compositions comprise hawthorn fruit (Shan Zha), light wheat grain (Fu xiao mai) and Lilly Bulb (bai hi) in amounts which are effective to treat anxiety conditions. The compositions may further comprise Chinese date (Da zao).

11 Claims, 5 Drawing Sheets

(56) References Cited

OTHER PUBLICATIONS

Peng, W.H., Hsieh, M.T., Lee, Y.S., Lin, Y.C., Liao, J., Anxiolytic effect of seed of Ziziphus jujuba in mouse models of anxiety., Journal of Ethnopharmacology, 2000, pp. 435-441, vol. 72, Elsevier, Netherlands.

Prenner L., Sieben A., Zeller K., Weiser D., Haberlein H., Reduction of high-affinity beta2-adrenergic receptor binding by hyperforin and hyperoside on rat C6 glioblastoma cells measured by fluorescence correlation spectroscopy. Biochemistry, 2007, pp. 5106-5113, vol. 46, American Chemical Society, United States.

Qin Zhu et al., Observations on the Therapeutic Effects of Treating 68 Cases of Examination Anxiety with Gan Mai Da Zao Tang (Licorice, Wheat & Red Date Decoction) Combined with Daoist Cognitive Therapy, 2003, pp. 29-30, vol. 12, Blue Poppy Enterprises (abstract only).

Sheehan D.V., Sheehan K.H., Current approaches to the pharmacologic treatment of anxiety disorders, Psychopharmacology Bulletin, 2007, pp. 98-99, vol. 40, No. 1, United States.

Vasa R.A., Pine D.S, Masten C.L., Vythilingam M., Collin C., Charney D.S. et al., Effects of yohimbine and hydrocortisone on panic symptoms, autonomic responses, and attention to threat in healthy adults, Psychopharmacology, 2009, pp. 445-455, vol. 204, No. 3, Berlin.

Wildmann J., Vetter W., Ranalder U.B., Schmidt K., Maurer R., Mohler H., Occurrence of pharmacologically active benzodiazepines in trace amounts in wheat and potato. Biochemical Pharmacology, 1988, pp. 3549-3559 vol. 37, No. 19, Pergamon Press, Great Britian.

Wong, M. L. & Licinio, J., From monoamines to genomic targets: a paradigm shift to drug discovery in depression. Nature Review. Drug Discovery, 2004, pp. 136-151, vol. 3, United States.

* cited by examiner ated with many side-effects (Wong & Licinio, 2004). Benzodiazepines, which act by increasing the inhibitory actions of GABA (gamma-aminobutyric acid), are an effective treatment for anxiety disorders, but have a major problem. These agents are prescribed for short periods only to avoid developing tolerance and physical dependence. However, the chronic nature of anxiety disorders requires long-term treatment. This problem prompted research to assess the efficacy of other agents (Barbui & Cipriani, 2009).

HERBAL COMPOSITION FOR TREATING ANXIETY RELATED CONDITIONS

FIELD OF THE INVENTION

This invention relates to a novel pharmaceutical and nutritional composition based on herbal mixture, and its use in a method of treating anxiety and stress.

BACKGROUND OF THE INVENTION

Anxiety disorders are among the ten most important public health concerns, according to the World Health Organization (WHO) and, in recent years, reached epidemic proportions. According to the American National Institute of Mental Health statistics, anxiety disorders affect up to 19 million North American adults. Results from the Israel National Health Survey indicate that 17% of adult population in Israel reported a lifetime occurrence of a mood or anxiety disorder.

Current treatments for anxiety disorders are of limited efficacy in a considerable proportion of patients and are associated with many side-effects (Wong & Licinio, 2004). Benzodiazepines, which act by increasing the inhibitory actions of GABA (gamma-aminobutyric acid), are an effective treatment for anxiety disorders, but have a major problem. These agents are prescribed for short periods only to avoid developing tolerance and physical dependence. However, the chronic nature of anxiety disorders requires long-term treatment. This problem prompted research to assess the efficacy of other agents (Barbui & Cipriani, 2009).

It has been demonstrated that selective serotonin reuptake inhibitors, SSRIs (such as Fluoxetine, Citalopram, Paroxetine), are effective in treating a wide spectrum of anxiety disorders, and may be used as a chronic treatment. However, recent studies show that their success rates for treating anxiety disorders are not high, reaching 50% at most (Pelissolo, 2008). In addition, despite their therapeutic actions, SSRIs are also associated with a wide variety of side effects such as sexual dysfunction, weight changes, insomnia, drowsiness or sedation, agitation, fatigue, dry mouth, gastrointestinal disturbances, and headache (Dording et al., 2002).

A traditional Chinese compound commonly known as "Gan Mai Da Zao Tang" containing Chinese date, wheat grains and licorice root (gan cao) was found by modern pharmacological researches to have sedative and soporific effects, combat fright, relax smooth muscle contractions, and regulate the autonomic nervous system. This compound was found to have a therapeutic effect when treating patients with anxiety disorders (Qin Zhu et al., 2003).

In light of the evidence reviewed above, the need for an anxiety-specific as well as side-effect-free drug is evident.

SUMMARY OF THE INVENTION

The present invention is based on the finding that a novel herbal mixture comprising adaptogens demonstrated an anxiolytic effect in various animal models of stress.

Accordingly, in a first of its aspects, the present invention provides pharmaceutical or nutritional compositions comprising hawthorn fruit (Shan Zha), light wheat grain (Fu xiao mai) and Lilly Bulb (bai hi) for the treatment of anxiety disorders or stress.

In one embodiment, the composition of the invention comprises hawthorn fruit in the amount of about 33.3% by weight of the composition, light wheat grain in the amount of about 33.3% by weight of the composition, and Lilly Bulb in the amount of about 33.3% by weight of the composition. In one embodiment the composition of the invention further comprises Chinese date (Da zao).

In another embodiment, the composition of the invention comprises hawthorn fruit in the amount of about 25% by weight of the composition, light wheat grain in the amount of about 25% by weight of the composition, Lilly Bulb in the amount of about 25% by weight of the composition and Chinese date in the amount of about 25% by weight of the composition.

In another embodiment, the composition of the invention comprises hawthorn fruit in the amount of about 10% by weight of the composition, light wheat grain in the amount of about 30% by weight of the composition, Lilly Bulb in the amount of about 30% by weight of the composition and Chinese date in the amount of about 30% by weight of the composition.

In one embodiment, the composition further comprises DMSO.

In another embodiment, the compositions are provided to a subject in need thereof in an amount of about 1 g/day to about 15 g/day. In certain embodiments subjects receive about 6 g/day to about 12 g/day, or about 6 g/day to about 9 g/day. In other embodiments, the compositions are provided in an amount of about 1 g/day, 2 g/day, 3 g/day, 4 g/day, 5 g/day, 6 g/day, 7 g/day, 8 g/day, 9 g/day, 10 g/day, 11 g/day, 12 g/day, 13 g/day, 14 g/day, or 15 g/day. In one specific embodiment said subject is human.

In certain embodiments the composition of the invention further comprises an additional herbal component having calming or anxiolytic effects.

In certain embodiments the composition of the invention further comprises additional active ingredients selected from the group consisting of antioxidants or vitamins. In a further embodiment, the compositions of the invention are suitable for oral or parenteral administration.

The compositions of the invention may be in the form selected from the group consisting of a tablet, a capsule, a liquid, a tincture, syrup, a powder, and raw herbs decoction. The compositions of the invention may also be encapsulated within a microcapsule, according to methods well known in the art, for example in a liposome or a micelle.

The compositions of the invention may cause an increase in the level of BDNF in the brain of a treated patient, and/or an increase in the level of cortisol in the blood of the treated patient.

Measurement of cortisol level in the patient's blood may serve as an indicator to the success of the treatment.

In another aspect, the present invention provides a method of treating anxiety disorders or stress comprising administering to a patient in need thereof an effective amount of the pharmaceutical compositions of the invention.

In another aspect, the present invention provides use of hawthorn fruit, light wheat grain and Lilly Bulb in the preparation of a pharmaceutical or nutritional composition for the treatment of anxiety disorders or stress. In certain embodiments said pharmaceutical composition further comprises Chinese date.

BRIEF DESCRIPTION OF THE DRAWINGS

In order to understand the invention and to see how it may be carried out in practice, embodiments will now be described, by way of non-limiting example only, with reference to the accompanying drawings, in which.

Vehicle—negative control group injected with the carrier solution; Adaptogens Treatment—treatment group (n=12) treated with the adaptogen composition of the invention; escitalopram—positive control group treated with a known anxiolytic drug.

FIG. 2 is a graph demonstrating the effect of treatment (Adaptogenic mixture n=12, escitalopram n=12, vehicle n=12) on anxiety-related behaviors in BALB mice in 3 treatment time points, following acute stress (Yohimibine injection i.p 1.25 mg/kg). FIG. 2A: Effect of treatment in the novel open field Test following one week of treatment. FIG. 2B: Effect of treatment in the novel open field Test following two weeks of treatment. FIG. 2C: Effect of treatment in the novel open field Test following three weeks of treatment—the time spent inside the field of the control group is significantly less pronounced in comparison to the group treated with the adaptogenic mixture (p<0.05) and with the group treated with escitalopram (p<0.0.1). FIG. 2D: Effect of treatment in the Elevated Plus Maze following three weeks of treatment—the time spent in the open arms of the group treated with the adaptogenic mixture is significantly more pronounced in comparison to the control group (p<0.05).

Figure 3:
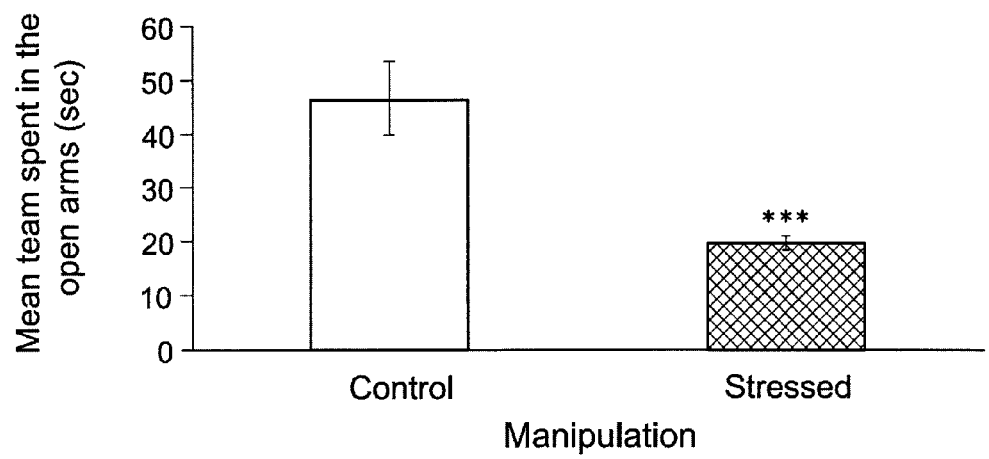

FIG. 3 is a graph showing the effect of an anxiety model (subjection to maternal separation in the postnatal period and unpredictable chronic mild stress in adolescences) on anxiety-related behavior. The time spent in open arms was significantly more pronounced in the control group in comparison to stressed mice (p<0.001).

Figure 4:
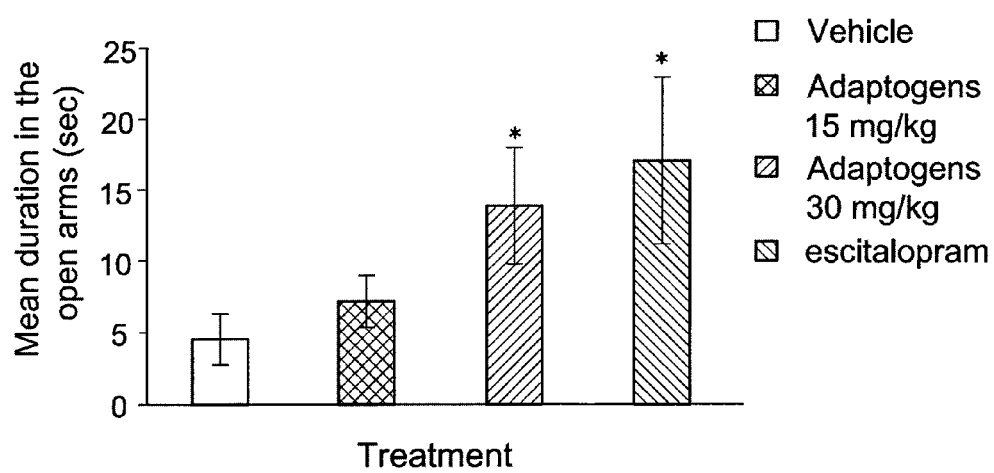

FIG. 4 is a graph showing the time spent in the open arms of the Elevated Plus Maze.

Figure 5:
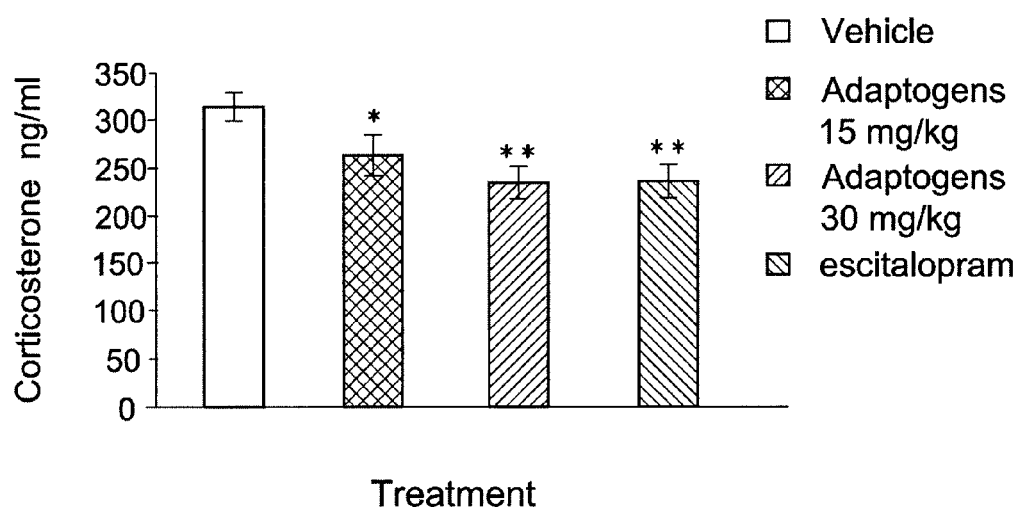

FIG. 5 is a graph showing corticosterone levels following acute restraint stress.

Figure 6A:
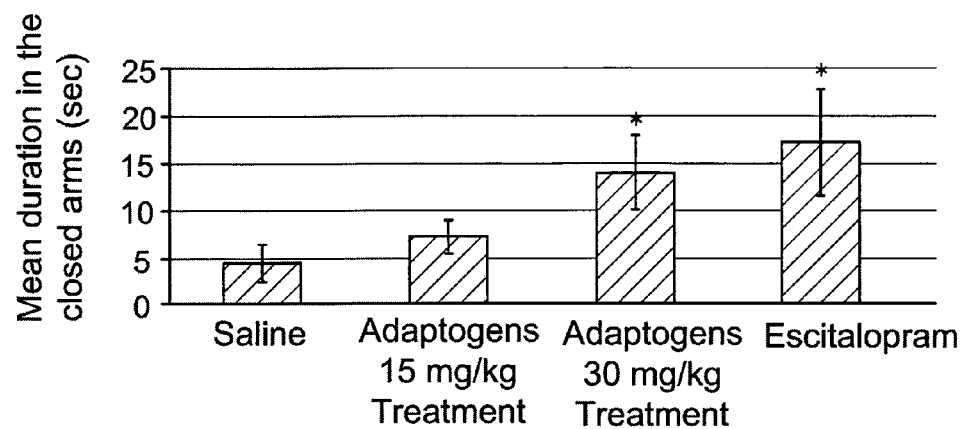

FIG. 6A is a graph demonstrating treatment effect in the Elevated Plus Maze—the time spent in the open arms by the group treated with the adaptogenic mixture (30 mg/kg) is significantly more pronounced in comparison with the control group (p<0.05), the same effect was noted in the escitalopram treated group (p<0.05).

Figure 6B:
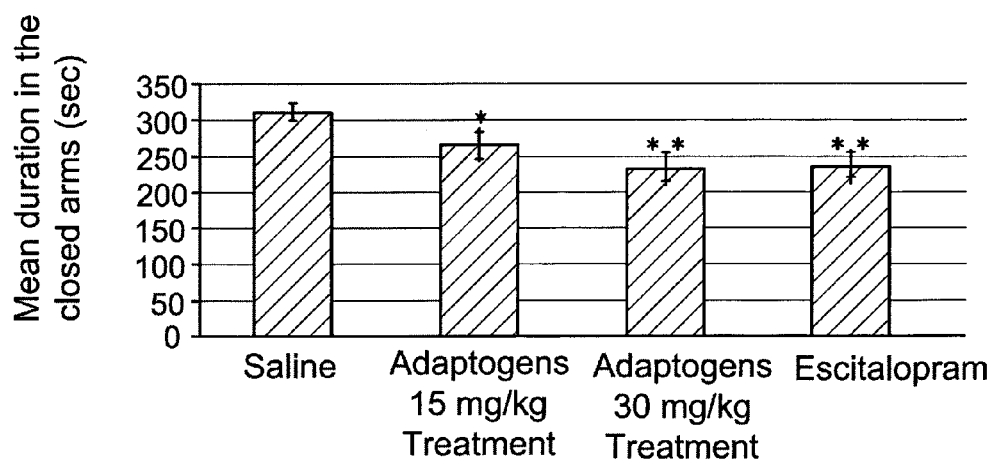

FIG. 6B is a graph demonstrating Corticosterone levels following acute restraint stress: The group treated with the adaptogenic mixture had significantly lower corticosterone levels in comparison to the control group (p<0.01 for 30 mg/kg and p<0.05 for 15 mg/kg), the same effect was noted in the escitalopram treated group (p<0.01).

DETAILED DESCRIPTION OF EMBODIMENTS

The present invention is based on the use of a novel combination of adaptogens in the treatment of anxiety disorders.

As used herein the term "adaptogens" refers to plant-derived pharmaceutical agents that increase the ability of an organism to adapt to stressful and changing environmental factors (Panossian et al., 1999) while causing negligible or no side effects.

Phytochemical and behavioral studies demonstrated the therapeutic potential of chronic treatment with adaptogens in various disorders (Davydov & Krikorian, 2000; ESCOP Monographs, 2003a, b). The advantage of adaptogens is in offering a natural source for various clinically active substances, which is relatively safe according to practice in complimentary medicine. The pharmacological action of these drugs typically generates no side effects, in contrast to traditional stimulants. Adaptogens from herbal source do not exhibit such negative effects: These compounds act on the nervous system by mechanisms which differ from those of traditional stimulants. It is commonly used in traditional Chinese herbal medicine. The herbal source of adaptogens is usually edible plants and fruits.

The present invention thus relates to herbal compositions for the treatment and/or prevention of anxiety disorders or stress.

The herbal compositions of the invention are also referred to as the "adaptogenic compositions" of the invention.

The term "treatment" is used conventionally and refers to the management or care of a subject for the purpose of combating, alleviating, reducing, relieving or improving a subject's anxiety condition, stress or any symptom thereof. The term encompasses any reduction in the subject's anxiety condition or stress as evidenced, for example, by a subject's personal report, by suitable questionnaires, or by measurement of physiological indicators of anxiety e.g. blood cortisol levels, whereby high levels of cortisol are indicative of stress.

As used herein the term "anxiety disorders" refers to different forms of abnormal and pathological fear and anxiety. The term encompasses anxiety disorders characterized by continuous or episodic symptoms including generalized anxiety, phobic, and panic disorders. Anxiety disorders are characterized by mental apprehension, and various physical symptoms such as physical tension.

The novel herbal composition of the invention comprises at least three components: hawthorn fruit, light wheat grain, and Lilly Bulb.

The composition may further comprise Chinese date. The composition of the invention may also be a pharmaceutical composition or nutritional composition comprising hawthorn fruit, light wheat grain, and Lilly Bulb.

The pharmaceutical composition may further comprise Chinese date. As used herein the term "pharmaceutical composition" refers to the herbal composition of the invention wherein said herbal composition is provided as a medicament. As used herein the term "nutritional composition" refers to the herbal composition of the invention wherein said herbal composition is provided as a nutrition additive.

Hawthorn (also termed *Crataegus pinnatifida* or Shan Zha) fruit contains high levels of triterpene acids and the flavonoids hyperoside and isoquercitrin (Cui et al., 2006a), the active constituents that determine its physiological effects. Both flavonoids and triterpenes belong to the two main groups of adaptogen active elements. Chronic treatment of rats with hyperoside and isoquercitrin was found to down-regulate HPA-axis function by significantly reducing circulating ACTH and corticosterone levels (Butterweck et al., 2004). Hyperoside was also found to reduce β2-adrenergic receptor sensitivity in rat glial cultures (Prenner et al., 2007), similar to the antidepressant desipramine. Reports have shown that hawthorn extracts possess endothelium-dependent anti-stress vasorelaxation effects (Chen et al., 1998) and endothelin-1 (a vasoconstrictor) inhibitory action (Corder et al., 2004) due to high procyanidin levels.

Aqueous acid extracts of wheat grain (also termed *Triticum aestivum* or Fu Xiao Mai) were found to contain a series of compounds belonging to the classical 5-phenyl-1,4-benzodiazepinones which display high affinity to the central benzodiazepine receptor in the brain (Wildmann et al., 1988). One of the compounds was shown to be identical to diazepam, which mediates anxiolytic and muscle relaxant effects by acting on inhibitory GABAergic receptors (Chouinard, 2004). Animal studies support a hypnotic effect in rats that were treated with an herbal formula containing *Triticum aestivum, Radix glycyrrhizae* and *Fructus ziziphus*.

Lilly Bulb (also termed *Lilium brownii* or Bai he) is an adaptogen which exhibits high inhibitory activity and selectivity towards monoamine oxidase (MAO)-B, which catalyzes the oxidative deamination of biogenic monoamines, in rat brain homogenates (Lin et al., 2003). Inhibition of MAO-B elevates monoamine levels, which is the basis for the action of anti-depressant and anxiolytic treatments in the clinic, such as MAO inhibitors and SSRIs (Sheehan and Sheehan, 2007). In addition, selective MAO-B inhibitors, unlike non-selective MAOIs, do not cause tyramine accumulation and thus do not induce the dangerous hypertensive crisis (also known as the "cheese effect") (Sheehan and Sheehan, 2007). Studies show that *lilium* exerts immunomodulatory functions and may suppress overreactive immune responses (Ko and Leung, 2007). It also possesses antioxidant properties.

Fructus Zizyphi Jujubae (also termed Da Zao or Chinese date) has been used in traditional medicine to treat insomnia and anxiety. In modern pharmacological studies, Ziziphi Jujuba was shown to possess hypnotic-sedative, hypertensive, anti-hypoxia, and hypothermic effects. Studies on animal models of anxiety demonstrate that Ziztphi Jujubea possesses an anxiolytic effect at lower doses and a sedative effect at higher doses (Peng et al. 2000).

Use of three or more of the above described herbs as provided in the composition of the invention results in a synergistic effect of the composition which is significantly more effective in the treatment of anxiety and stress than that achieved by the use of each of these herbs as a single agent.

Any effective part of the herbs in accordance with the present invention can be used, including seeds, leaves, stems, flowers, roots, fruit, bark, or any other plant parts which are useful for the purposes described. Herbs can be in any form that is effective, including, but not limited to dry powders, grounds, emulsions, extracts, and other conventional compositions. To extract or concentrate the effective ingredients of a herb, typically the plant part is contacted with a suitable solvent, such as water or alcohol, or a mixture of several solvents. The choice of the solvent can be made routinely, e.g. based on the properties of the active ingredient that is to be extracted or concentrated by the solvent.

In one embodiment, the composition is dissolved in a salt solution (e.g. saline)+DMSO (dimethyl sulfoxide), preferably in 1% DMSO.

In one embodiment Hawthorn is used in the form of an extract of the fruit.

In one embodiment wheat grain is used in the form of an aqueous acid extract of the grains.

In one embodiment Lilly bulb is used in the form of an extract.

In one embodiment Zizyphi Jujubae is used in the form of an extract of the fruit.

In a specific embodiment the composition comprises equal ratios of the various adaptogens.

A composition of the invention can comprise the following ingredients by weight:
(a) hawthorn fruit in the amount of about 33.3% by weight of the composition,
(b) light wheat grain in the amount of about 33.3% by weight of the composition, and
(c) Lilly Bulb in the amount of about 33.3% by weight of the composition.

In another embodiment, the composition of the invention can comprise:
(a) hawthorn fruit in the amount of about 25% by weight of the composition,
(b) light wheat grain in the amount of about 25% by weight of the composition,
(c) Lilly Bulb in the amount of about 25% by weight of the composition, and
(d) Chinese date in the amount of about 25% by weight of the composition.

In another embodiment, the composition of the invention can comprise:
(a) hawthorn fruit in the amount of about 10% by weight of the composition,
(b) light wheat grain in the amount of about 30% by weight of the composition,
(c) Lilly Bulb in the amount of about 30% by weight of the composition, and
(d) Chinese date in the amount of about 30% by weight of the composition.

In certain embodiments the composition of the invention may comprise additional active ingredients appropriate for the treatment of anxiety, stress or other conditions. Such active ingredients may be obtained from herbs, minerals and other ingredients having calming or anxiolytic effects including, but not limited to:

Zhu Sha (cinnabaris)
Ci Shi (magnetitum)
Long Gu (os draconis)
Long Chi (dens draconis)
Mu Li (concha ostreae)
Hu Po (succinum)
Zhen Zhu (margarita)
Zhen Zhu Mu (concha margaritaferae)
Suan Zao Ren (semen zizyphi spinosae)
Bai Zi Ren (semen platycladi)
Yuan Zhi (radix polygalae)
He Huan Pi (cortex albiziae)
Ye Jiao Teng (caulis polygoni multiflori)
Ling Zhi (*ganoderma*)
Dan Shen (radix salviae miltiorrhizae)
Fu Shen (poria paradicis)
Lian Zi (semen nelumbinis)
Long Yan Rou (arillus longan)
Mai Men Dong (radix ophiopogonis)
Ren Shen (radix ginseng)
Shi Chang Pu (rhizoma acori)
Wu Wei Zi (fructus schisandrae chinensis)
Hong zao (Red date)

In certain embodiments the composition of the invention may further comprise additional active agents such as antioxidants (e.g. selenium), vitamins (such as vitamin A, B1, B2, thiamine, B6, pyridoxine, B complex, biotin, nicotinic acid, B12, C, ascorbic acid, D, D2, D3, E, riboflavin, K, K1 or K2), Co Enzyme Q10, NADH, NAD, D-ribose, or amino acids such as L-Glutamine or Lysine.

Compositions can further comprise inert and carrier ingredients, stabilizers, and surfactants including, but not limited to, water, salt solutions, alcohols, oils, gelatin, paraffin, carbohydrates such as lactose, amylase or starch, and fatty acids. Other additives that may be included in the composition are preservatives, coloring and flavoring agents, emulsifying and suspending agents such as acacia, agar, sodium alginate, cellulose, methylcellulose, cholesterol, and derivatives thereof, solvents, microcrystalline cellulose, citric acid, dextrin, dextrose, glucose, lactic acid, lactose, magnesium chloride and the like.

The composition of the invention can be administered alone, or in combination with other active agent(s). Compositions of the present invention may be combined with other treatments including behavioral therapy, diet restrictions and pharmacological intervention. Various drugs are known in the art for the treatment of anxiety disorders or stress, and these can be combined with the compositions of the present invention.

The present invention further provides a method of treating anxiety disorders or stress comprising administering to a patient in need thereof an effective amount of the composition of the invention.

The amounts of the ingredients in the composition are effective in alleviating anxiety or stress. An "effective amount" indicates that the mass of ingredients in the composition is useful to achieve the purpose for which it is administered. Amounts are selected based on various factors, including age, general health, gender, weight or severity of condition of a patient to be treated.

By the term "administered", it is meant that the composition is delivered to a subject by any means or route which is effective to achieve the desired result, including e.g. oral, parenteral, enteral, intraperitoneal, topical, transdermal (e.g. using any standard patch), subcutaneous, intravenous, intraarterial, intramuscular, buccal, sublingual, ophthalmic, nasal, by aerosol, by inhalation, rectal, vaginal and intrathecal.

In one embodiment the composition of the invention is administered to human subjects in an amount of about 5 to about 15 gram per day. In one specific embodiment the composition of the invention is administered to human subjects in an amount of about 6 to about 12 gram per day. In another specific embodiment the composition of the invention is administered to human subjects in an amount of about 6 to about 9 gram per day. The compositions can be administered 1, 2, 3, 4, 5, or 6, etc times a day, depending upon the subject's physical condition, the severity of disease, etc. Compositions can be administered at any suitable time, e.g. prior or after a meal, prior to activity, prior to sleeping and at different times of the day, e.g. in the morning, in the evening etc.

The composition of the invention can be formulated in a way suited to oral or parenteral administration in accordance with conventional techniques and excipients, as described for example in "Remington's Pharmaceutical Science Handbook", $17^{th}$ Ed Mack Pub. N.Y., U.S.A. Parenteral administration includes intraperitoneal (ip), subcutaneous (sc), intravenous (iv) and intramuscular (im) injection.

The following are examples of administration formulations: liquids and suspensions, extracts, injectable forms, sprays, inhalers, gel, emulsions, tablets, capsules, pills, suppositories, transdermal patches, granulates and powders. The compositions can also be included in food or beverage (e.g. tea). Gastro-protected and/or modified release formulations are suitable for oral administration, especially modified-release tablets which release the active ingredients in a prolonged and sustained manner, for example several hours (e.g. 5-8) following administration. Such prolonged-release tablets may be obtained by incorporation of polymers or copolymers commonly used for this purpose, such as acrylic copolymers or cellulose derivatives.

In certain embodiments the composition of the invention is used as a chronic treatment for anxiety disorders, or as a preemptive treatment for individuals exposed to conditions of mental or physical stress.

Studies in animal models of anxiety show that the composition of the invention provides an anxiolytic effect.

The following examples illustrate the invention in greater detail:

Example 1

Measurement of Anxiety-related Behavior in Rodents—The Elevated Plus-Maze (EPM)

A well known measurement of anxiety-related behavior in rodents is the Elevated Plus-Maze (EPM). The test setting consists of a plus-shaped apparatus with two open and two closed arms, each with an open roof, elevated 40-70 cm from the floor. The model is based on rodents' aversion of open spaces. This aversion leads to the behavior termed thigmotaxis, which involves avoidance of open areas by confining movements to enclosed spaces or to the edges of a bounded space. In EPM this translates into a restriction of movement to the enclosed arms. Anxiety reduction in the plus-maze is indicated by an increase in the time spent in the open arms.

Figure 1:
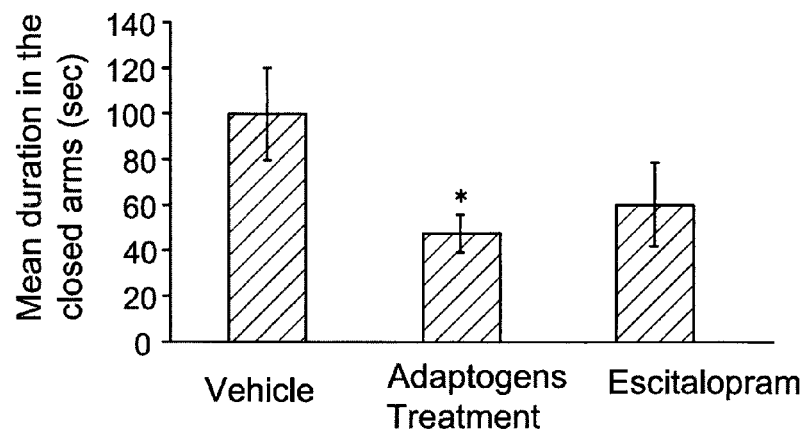
FIG. 1 is a graph demonstrating the effect of different treatments on anxiety-like behavior in BALB mice.
Figure 2A:
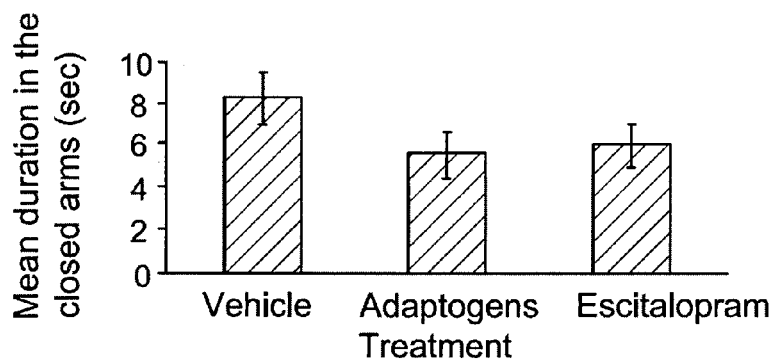
Figure 2B:
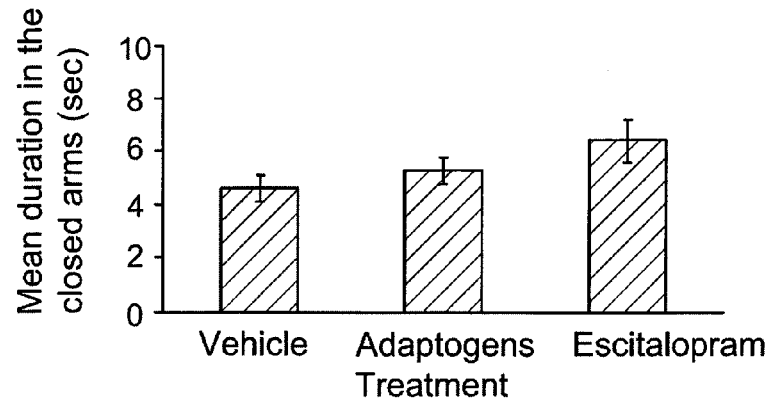
Figure 2C:
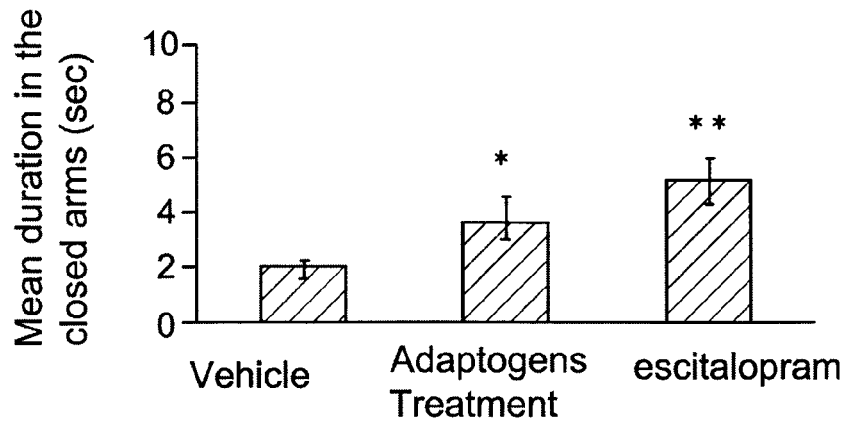
Figure 2D:
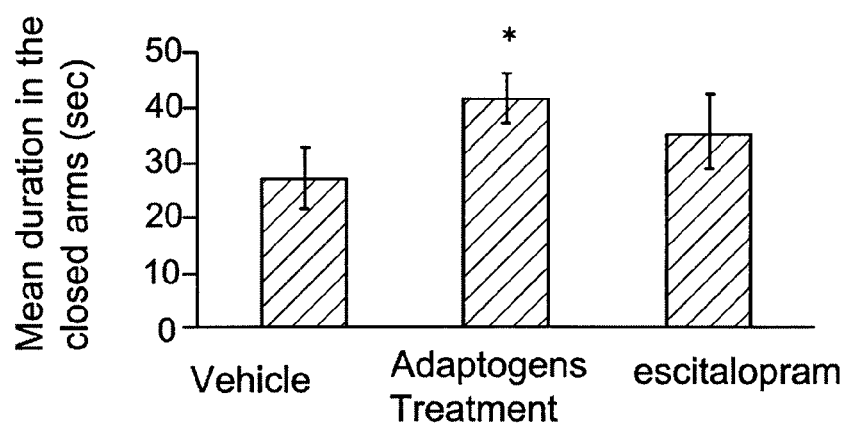

BALB mice (a strain known to exhibit increased anxiety-like behavior) were treated either with the adaptogenic composition of the invention (namely a mixture of Hawthorn fruit, wheat grain, Lilly Bulb and Zizyphi Jujubae in equal ratios) (10 mg/kg/day), with conventional treatment (escitalopram) or with the vehicle (Saline +1% DMSO) for the duration of 14 days via i.p. injection. Anxiolytic effect was assessed via the elevated plus maze. Results demonstrate an anxiolytic effect of the novel treatment; the time spent in the closed arms of the control group was significantly ($p<0.05$) more pronounced in comparison to the group treated with the adaptogenic mixture (n=12) (see FIG. 1).

Example 2

Measurement of Anxiety-related Behavior after Acute Episodic Stress

Another study conducted on BALB mice was aimed to examine the anxiolytic effect after acute episodic stress during the treatment and following 3 weeks of treatment. Mice were treated through i.p. injection with the adaptogenic mixture (15 mg/kg/day), escitalopram (15 mg/kg/day) or vehicle. The acute stress was obtained with Yohimibine i.p injection, a drug known to activate a stress-reaction (Vasa et al., 2009). Results demonstrate an anxiolytic effect of the adaptogenic treatment in the Elevated plus maze and in the novel open field (see FIG. 2).

The Novel Open Field is another well-established test of anxiety-related behavior in rodents. The Open Field area generally consists of an empty and bright square arena, surrounded by walls to prevent the rodent from escaping. The rodent is usually placed in the center of the arena and its behavior recorded over a chosen period. The Novel Open Field task approaches the conflict between the innate fear that rodents have of the central area of a novel or brightly lit open field versus their desire to explore new environments. When anxious, the natural tendency of rodents is to prefer staying close to the walls. In this context, anxiety-related behavior is measured by the degree to which the rodent avoids the center of the arena.

Example 3

Assessment of Stress Responses Following Chronic Stress

Animals

ICR outbred mice, purchased from 'Harlan, Israel', were bred and kept in an approved animal house at the 'Tel-Aviv Academic College' vivarium. The animals were housed in standard laboratory cages (transparent polycarbonate cages, Makrolon type III, 37.5×22×5 cm) in a colony room (T, 22±2° C.; relative humidity, ±60%). The floors of the cages were covered with a 2-3 cm thick layer of wood shavings. All procedures were carried out in accordance with the Israeli Council for Experimentation on Animal Subjects (ICEAS) institutionally approved protocols. Mice were given free access to food and soured water and were maintained on a 12 h light/dark cycle (lights off at 7 AM). All experiments were approved by the international committee for animal care and use in Israel (MTA-0001-4-07-10).

Maternal Separation (MS)

On the day of parturition, PND 0 (postnatal day), litters were randomly assigned to undergo MS or to be standard facility reared (SFR) controls. SFR animals were left undisturbed during the entire stress manipulation (both maternal separation and unpredictable chronic mild stress manipulation), except for routine cage maintenance performed once a week. MS procedure was carried out once per day from PND 1-14. The MS procedure was performed by removing the pups from the home cage and placing them together in a separate clean cage placed on a heating pad (30-33° C.) in order to keep the pups in a temperature close to the dam's natural body temperature. 6 hours later, pups were returned to their home cage. At the age of 21 days, all pups were weaned and sexed, while the male mice were separated into cages of five mice per cage.

Unpredictable Chronic Mild Stress (UCMS)

The chronic stress procedure was performed on the MS group during adolescence, from the age of 4 and 7 weeks. All the mice were subjected several times a day for 3 weeks to one of the following stressors such as forced swim in water, placement in an empty cage with water at the bottom, inducing social stress by swapping soiled cages of separated group of mice, inversion of light/dark cycle, lights on for a short period of time during the dark phase as well as being restrained. To prevent habituation and to provide an unpredictable feature to the stressors, all the stressors were administered at different time points of the day (see table 1).

treated with a conventional anxiolytic drug—escitalopram (15 mg/kg) and a control group, receiving only the vehicle. Drug administration was given through i.p. injection of the relevant drug or vehicle for the duration of 21 days.

Drugs

Adaptogenic mixture: As mentioned before, the adaptogenic mixture was made out of those four components: *Crataegus pinnatifida, Triticum aestivum, Lilium brownii* and Fructus Zizyphi Jujubae. Same proportions of concentrated powder extracts of each of the components, processed as freeze-dried granules, were dissolved in Saline and 1% DMSO.

Conventional treatment: The conventional treatment that was used is Escitalopram—a potent, well tolerated SSRI with anxiolytic-like effects. 15 mg/kg/day dosage given through intraperitoneal (i.p.) injection is known to have an anxiolytic effect on ICR mice. Concentrated powder of Escitalopram was dissolved in Saline and DMSO 1%.

The Behavioral Phenotype: Assessment of Stress Responses Following Treatment

Following 3 weeks of treatment, all the treated groups were tested for anxiety-like behavior using the elevated plus-maze in order to assess the efficiency of the treatment on the behavioral phenotype.

The Biological Phenotype: Markers of Stress System Activity Following Treatment

In order to estimate the endocrinology reaction to acute stress mice were first placed in restraint. Restraint stress is a well documented stressor that initiates an acute transient increase in plasma ACTH and Corticosterone, usually peaking during the course of a 60 min stress exposure. Therefore, following 60 minutes of subjection to restraint stress, blood

TABLE 1 stressors administration:

| | Day 1 | Day 2 | Day 3 | Day 4 | Day 5 | Day 6 | Day 7 |
|---|---|---|---|---|---|---|---|
| Week 1 | Succession of four light/dark cycles every 30 min Social Stress (4 hours) | Placement in an empty cage with water at the bottom + Lights on (4 hours) | Succession of four light/dark cycles every 30 min Social Stress (4 hours) | Restraint stress (4 hours) | Placement in an empty cage with water at the bottom + Lights on (4 hours) | Restraint stress (4 hours) | Reversal of the light/dark cycle |
| Week 2 | Placement in an empty cage with water at the bottom + Lights on (4 hours) | Restraint stress (4 hours) | Succession of four light/dark cycles every 30 min Social Stress (4 hours) | Restraint stress (4 hours) | Placement in an empty cage with water at the bottom + Lights on (4 hours) | Restraint stress (4 hours) | Reversal of the light/dark cycle |
| Week 3 | Placement in an empty cage with water at the bottom + Lights on (4 hours) | Restraint stress (4 hours) | Succession of four light/dark cycles every 30 min Social Stress (4 hours) | Placement in an empty cage with water at the bottom + Lights on (4 hours) | Restraint stress (4 hours) | Placement in an empty cage with water at the bottom + Lights on (4 hours) | Reversal of the light/dark cycle |

The Behavioral Phenotype: Assessment of Stress Responses

Elevated plus-maze: Each mouse was placed in the center of the elevated plus maze and his behavior was recorded for the duration of 5 minutes.

Treatment of EXPERIMENTAL AND CONTROL GROUPS

"Stressed" mice were randomly assigned to 4 groups of treatment: 2 groups receiving different dosage of the adaptogenic mixture (15, 30 mg/kg), a positive control group, samples were collected into EDTA-coated tubes from the facial vein. All blood samples were kept on ice and later centrifuged for 10 min at 10000 rpm at 4°. Plasma was transferred to clean, labeled 1.5 ml microcentrifuge tubes. All plasma samples were stored frozen at −20 C.° until the determination of Corticosterone via RIA.

Experimental Design

On the day of parturition (PND 0) litters were randomly assigned to undergo stress manipulations (n=80) or to standard facility reared (SFR) controls (n=15). "Stressed" group was assigned to undergo maternal separation paradigm for the duration of 14 days while the SFR were left undisturbed. At the age of 21 days all pups were weaned and sexed, and the male mice were separated into cages of five mice per cage. Between the age of 28 and 56 days (Adolescence) "stressed" mice were subjected to Unpredictable Chronic Mild Stress paradigm, as previously described while the SFR were left undisturbed.

Subsequent to the stress manipulations, anxiety-like behavior was assessed via the elevated plus maze in order to assess the effect of the stress manipulations. Thereafter, "stressed" mice were randomly assigned into various groups of treatment as previously described. Following three weeks of treatment with the relevant drug or vehicle, anxiety-like behavior was assessed via the elevated plus maze. 48 hours thereafter and while mice were still receiving treatment, blood samples were collected following acute stress and Corticosterone levels were measured via radio immunoassay (RIA) assay.

The Behavioral Phenotype: Assessment of Stress Responses

Behavioral alterations following chronic stress were assessed via the elevated plus maze (FIG. 3); Control animals spent more time in the open arms in comparison to animals from the chronic stress group ($p<0.001$, t-test).

The Behavioral Phenotype: Assessment of Stress Responses Following Treatment

Behavioral alterations following chronic treatment with the adaptogenic treatment were assessed via the elevated plus maze (FIG. 4); Treated groups (adaptogenic mixture 30 mg/kg and escitalopram) spent significantly more time in the open arms in comparison to control group ($p<0.05$, t-test), the same effect that was noted in the escitalopram treated group.

The Biological Phenotype: Markers of Stress System Activity Following Treatment

Corticosterone levels (FIG. 5) of all treated groups was significantly lower in comparison to control group ($p<0.01$ for 30 mg/kg and $p<0.05$ for 15 mg/kg). The group treated with the adaptogenic mixture had significantly lower corticosterone levels in comparison to the control group ($p<0.01$ for 30 mg/kg and $p<0.05$ for 15 mg/kg), the same effect that was noted in the escitalopram treated group ($p<0.01$).

Example 4

Measurement of Anxiety-related Hormonal Indicators

Another study was aimed to assess the anxiolytic effect of the adaptogenic mixture on hormonal indicators.

Stress in humans and a variety of animal species induces the release of corticotropin-releasing hormone (CRH) from the Hypothalamus. CRH then activates anterior pituitary cells to release adrenocorticotropic hormone (ACTH), which in turn activates the adrenal cortex to secrete glucocorticoid hormones such as cortisol in humans and corticosterone in rodents (McEwen, 1998). Therefore, it is possible to assess anxiety through measurement of serum corticosterone levels.

ICR mice were subjected to maternal separation paradigm during the postnatal period and to unpredictable chronic mild stress paradigm in adolescence. Anxiety-related behaviors were assessed using the elevated-plus maze and indicated anxiogenic effect of the stress manipulation. During adulthood, mice were assigned to different groups of treatment: adaptogenic treatment (15, 30 mg/kg), escitalopram (15 mg/kg) and a control group, receiving only the vehicle. Following 3 weeks of treatment, behavioral assessments were performed. In addition, blood samples were collected following acute stress (restraint stress) and corticosterone levels were measured via RIA. In addition to attenuation of anxiety-like behavior, when confronted with acute stress, mice treated with the adaptogenic mixture exhibited a moderate hormonal reaction in comparison to the control group (see FIG. 6).

Interestingly, BDNF (brain derived neurotrophic factor) in the hippocampus of control mice were found to be significantly lower in comparison to mice treated with the adaptogenic composition of the invention.

Example 5

Effects of Treatment During Stress

Experimental Design

The day following parturition, postnatal day (PND) 1, the litters underwent a Maternal Separation (MS) procedure that was carried out once a day from PND 1-14. At the age of 21 days, all pups were weaned and sexed. 90 male mice were tagged, weighed, and separated into cages of up to five mice per cage, assigned randomly into four groups of treatment as previously described. Between the age of 28 and 56 days (Adolescence), mice were subjected to an Unpredictable Mild Stress paradigm. In this experiment three different stressors were used—all mice were subjected once a day to one of the following stressors: restrainers; placement in an empty cage with water at the bottom; or inversion of light/dark cycle. To prevent habituation and to provide an unpredictable feature to the stressors, every day different stressor was administered for four hours, at different time points of the day. During the entire stress paradigm, drugs were administrated through i.p. injection of the relevant treatment, for the duration of 28 days. Upon reaching adulthood and following four weeks of treatment, behavior, peripheral hormones and brain monoamines were measured in order to assess the effects of the novel treatment.

Behavior Tests

Following four weeks of treatment, all the treated groups were tested for anxiety-like behavior using the elevated plus-maze and a different version of the open field test, in order to assess the efficiency of the treatment on the behavioral phenotype.

The plus—maze was used in the same format as described above.

In addition to the behavior test, and prior to them, all the treated groups were subjected to Sucrose Test. The animals were separated to individual cages—one mouse per cage. In every cage, in addition to the ordinary sterilized water, another bottle was placed with sucrose diluted in sterilized water. The two bottles were left in the cage for 12 hours. The two bottles and the food of a particular cage were weighted. After the 12 hours, the amount of ordinary water, sucrose water and food eaten by the mouse, was calculated. The rational for this test is in the innate preference of the mice for sweet tastes and the known anxiety symptom of anhedonia. Thus, for the more anxious mice the expectation was that they will drink less sucrose water, showing no preference to the sweet taste in comparison to the ordinary water, and will eat less food than the less anxious mice.

Physiological Measurements

In order to estimate the endocrinological reaction to acute stress, mice were first placed in restrainers. Restraint stress is known to initiate an acute transient increase in plasma ACTH and Corticosterone, usually peaking during the course of a 60 min stress exposure. Therefore, following 60 minutes of subjection to restraint stress, blood samples were collected into EDTA-coated tubes from the facial vein. All blood samples were kept on ice and later centrifuged for 10 min at 10000 rpm at 4°. Plasma was transferred to clean, labeled 1.5 ml microcentrifuge tubes. All plasma samples were stored frozen at −20 C.° until the determination of Corticosterone via RIA.

At the end of the experiment, all treated mice were sacrificed. The brains of the mice were placed in a mold on ice. Serial sections were cut onto slides. Tissue punches of the hippocampus were taken. Extractions were achieved by sonication in 0.5 ml of a perchlorate solution (0.1M) containing EDTA/ethanol. Brain-derived neurotrophic factor (BDNF) was measured by EIA. It has been shown that stress and antidepressants have opposite effects on hippocampal BDNF expression, while stress can lead to neuronal atrophy and loss in several brain regions including the hippocampus, antidepressants may exert their therapeutic effect by increasing BDNF expression, thereby leading to the reversal of neuronal atrophy and cell loss.

Statistical Analysis

Paired t-tests as well as one-way ANOVA were conducted between all test groups for each of the behavioral variables. Later, post-hoc analyses using the Scheffé post-hoc criterion for significance were performed.

Results

In the Elevated Plus Maze test the time spent in the open arms by the two groups treated with the adaptogenic mixture in both doses (15 and 30 mg/kg) is significantly more pronounced in comparison to the control group ($p<0.05$), the same effect that was noted in the escitalopram treated group ($p<0.05$): 62 seconds in the group receiving 15 mg/kg adaptogens, 68 seconds in the group receiving 30 mg/kg adaptogens, and 64 seconds in the group receiving escitalopram, as compared with 44 seconds in the control group receiving saline.

In the sucrose test, sucrose consumption by the group treated with the adaptogenic mixture (30 mg/kg) is significantly more pronounced in comparison to the control group ($p<0.05$); the same effect that was noted in the escitalopram treated group ($p<0.05$): 56 ml were consumed in the group receiving 30 mg/kg adaptogens, and 55 ml in the group receiving escitalopram, as compared with 51 ml in the control group receiving saline.

Corticosterone levels following acute restraint stress: The group treated with the adaptogenic mixture (30 mg/kg) had significantly lower corticosterone levels (79.7 ng/ml) in comparison to the control group (80.9 ng/ml); the same effect was noted in the escitalopram treated group (77.3 ng/ml) ($p<0.05$).

In the measurements of BDNF levels, the results yield that the 30 mg\kg adaptogenic mixture group and the escitalopam group had significantly higher BDNF levels in comparison to control group: 17 pc/µg for the 30 mg/kg adaptogenic mixture group ($p<0.01$) and 16 pc/µg for the escitalopram group ($p<0.05$), as compared with 12 pc/µg for the control group (saline).

In conclusion, treatment with the composition of the invention either after or during the stress period significantly alleviates various behavioral and physiological symptoms of stress.

Example 6

Treatment of Anxiety-Related Conditions in Human Subjects

Human subjects (about 100) suffering from anxiety were treated with the adaptogenic composition of the invention (namely a mixture of Hawthorn fruit, wheat grain, Lilly Bulb and Zizyphi Jujubae in equal ratios) in an amount ranging from 6-12 g/day, most subjects received 6-9 g/day, daily for periods of several months (at least 6 months). The composition was provided in the form of powder for oral consumption. In certain instances, the powder was encapsulated and provided in the form of a tablet. About 65% success was reported in alleviating anxiety.

Example 7

Anxiolytic Effect of a Composition Comprising Hawthorn Fruit, Wheat Grain and Lilly Bulb C57BL/6 male and female infant mice were subjected to chronic stress (MSP) by separation from the dam for 6 hours per day from day 1 to day 14. Anxiety behavior was tested after different anxiolytic treatments. The mice received a daily i.p. injection from day 28 of age for two weeks, of one of the following drugs: Citalopram (10 mg/kg), or the adaptogenic composition of the invention comprising Hawthorn fruit, wheat grain and Lilly Bulb (10 mg/kg). The anxiety behavior was tested in the Open Field Test.

MSP mice treated with the composition of the invention spent significantly more time inside the center of the arena (6 seconds) compared with the Citalopram-treated group (2.5 seconds) and the saline-treated control group (1.8 seconds). $P<0.05$, n=16.

In addition, MSP mice treated with the composition of the invention entered significantly more times to the inside of the arena (4.4 times) compared with the Citalopram-treated group (2.4 times) and the saline-treated control group (1.6 times). $P<0.05$, n=16.

Moreover, MSP mice treated with the composition of the invention spent significantly more time inside the center of the arena (6 seconds) compared with the treated, unstressed group (4 seconds). On the other hand MSP mice treated with citalopram spent significantly less time inside the center of the arena (2.5 seconds) compared to unstressed mice (4.6 seconds). Similarly, MSP mice treated with saline also spent significantly less time inside the center of the arena (1.8 seconds) compared to unstressed mice (4.5 seconds).

Interestingly, MSP mice treated with the composition of the invention demonstrate less anxiety symptoms than mice which were not exposed to chronic stress at infancy.

REFERENCES

1. Barbui C., Cipriani A. (2009). Review: maintenance antidepressants reduce risk of relapse but effect is not as great in recurrent depression, *British Medical Journal*, 12, 79.
2. Butterweck V., Hegger M., Winterhoff H. (2004). Flavonoids of St. John's Wort reduce HPA axis function in the rat. *Planta Med*, 70, 1008-1011.
3. Chen Z. Y., Zhang Z. S., Kwan K. Y., Zhu M., Ho W. K., Huang Y. (1998). Endothelium-dependent relaxation induced by hawthorn extract in rat mesenteric artery. *Life Sci*, 63, 1983-1991.
4. Chouinard G. (2004). Issues in the clinical use of benzodiazepines: potency, withdrawal, and rebound, *J Clin Psychiatry*, 65, 7-12.
5. Corder R., Warburton R. C., Khan N. Q., Brown R. E., Wood E. G., Lees D. M. (2004). The procyanidin-induced pseudo laminar shear stress response: a new concept for the reversal of endothelial dysfunction. *Clin Sci (Loud)*, 107, 513-517.

6. Cui T., Nakamura K., Tian S., Kayahara H., Tian Y. L. (2006a). Polyphenolic content and physiological activities of Chinese hawthorn extracts. *Biosci Biotechnol Biochem* 70, 2948-2956.
7. Davydov M, Krikorian A D (2000) *Eleutherococcus senticosus* (Rupr. & Maxim.) Maxim. (Araliaceae) as an adaptogen: a closer look. *J Ethnopharmacol* 72:345-393.
8. Dording C. M., Mischoulon D., Petersen T. J., Kornblum R., Gordon J., Nierenberg A. A., Rosenbaum J. F., Fava M. (2002). The pharmacologic management of SSRI-induced side effects: a survey of psychiatrists. *Annals of Clinical Psychiatry,* 14, 143-147.
9. Ko K. M., Leung H. Y. (2007) Enhancement of ATP generation capacity, antioxidant activity and immunomodulatory activities by Chinese Yang and Yin tonifying herbs. *Chin Med,* 2, 3.
10. Lin R. D., Hou W. C., Yen K. Y., Lee M. H. (2003) Inhibition of monoamine oxidase B (MAO-B) by Chinese herbal medicines, *Phytomedicine,* 10, 650-656.
11. McEwen B. S. (1998b). Protective and damaging effects of stress mediators. *N Engl J Med,* 338, 171-179.
12. Panossian A., Gabrielian E., Wagner H. (1999). On the mechanism of action of plant adaptogens with particular reference to cucurbitacin R diglucoside. *Phytomedicine,* 6, 147-155.
13. Pelissolo. A., (2008) Efficacy and tolerability of escitalopram in anxiety disorders: a review. *Ecephale.* 34, 8-400.
14. Peng, W. H., Hsieh, M. T., Lee, Y. S., Lin, Y. C., Liao, J., 2000. Anxiolytic effect of seed of *Ziziphus jujuba* in mouse models of anxiety. *Journal of Ethnopharmacology,* 72, 435-441.
15. Prenner L., Sieben A., Zeller K., Weiser D., Haberlein H. (2007). Reduction of high-affinity beta2-adrenergic receptor binding by hyperforin and hyperoside on rat C6 glioblastoma cells measured by fluorescence correlation spectroscopy. *Biochemistry* 46, 5106-5113.
16. Qin Zhu et al. (2003). Observations on the Therapeutic Effects of Treating 68 Cases of Examination Anxiety with Gan Mai Da Zao Tang (Licorice, Wheat & Red Date Decoction) Combined with Daoist Cognitive Therapy. *Xin Zhong Yi* (*New Chinese Medicine*), 12, 29-30.
17. Sheehan D. V., Sheehan K. H. (2007). Current approaches to the pharmacologic treatment of anxiety disorders, *Psychopharmacol Bull,* 40, 98-109.
18. Vasa R. A., Pine D. S, Masten C. L., Vythilingam M., Collin C., Charney D. S. et al. (2009). Effects of yohimbine and hydrocortisone on panic symptoms, autonomic responses, and attention to threat in healthy adults, *Psychopharmacology,* 204, 445-455.
19. Wildmann J., Vetter W., Ranalder U. B., Schmidt K., Maurer R., Mohler H. (1988). Occurrence of pharmacologically active benzodiazepines in trace amounts in wheat and potato. *Biochem Pharmacol,* 37, 3549-3559.
20. Wong, M. L. & Licinio, J. (2004). From monoamines to genomic targets: a paradigm shift to drug discovery in depression. *Nature Review. Drug Discovery,* 3, 136-151.

The invention claimed is:

1. A pharmaceutical or nutritional composition for the treatment of anxiety disorders or stress, consisting of effective amounts of hawthorn fruit, light wheat grain and Lilly Bulb, and optionally, effective amounts of Chinese date, antioxidants, vitamins, and/or DMSO, and optionally an inert carrier, stabilizer, and/or surfactants.

2. The composition of claim 1, wherein the hawthorn fruit is in the amount of about 33.3% by weight of the composition, the light wheat grain is in the amount of about 33.3% by weight of the composition, and the Lilly Bulb is in the amount of about 33.3% by weight of the composition.

3. The composition of claim 1, wherein the hawthorn fruit is in the amount of about 25% by weight of the composition, the light wheat grain is in the amount of about 25% by weight of the composition, the Lilly Bulb is in the amount of about 25% by weight of the composition and the Chinese date is in the amount of about 25% by weight of the composition.

4. The composition of claim 1, wherein the hawthorn fruit is in the amount of about 10% by weight of the composition, the light wheat grain is in the amount of about 30% by weight of the composition, the Lilly Bulb is in the amount of about 30% by weight of the composition and the Chinese date is in the amount of about 30% by weight of the composition.

5. The composition of claim 1, formulated to be suitable for oral or parenteral administration.

6. The composition of claim 1, in the form selected from the group consisting of a tablet, a capsule, a liquid, syrup, tincture, powder, and raw herbs decoction.

7. The composition of claim 1, which is encapsulated within a microcapsule.

8. The composition of claim 7, wherein said microcapsule is a liposome or a micelle.

9. A method of treating anxiety disorders or stress, comprising administering to a patient in need thereof an effective amount of a pharmaceutical composition according to claim 1, wherein said amounts are effective to treat anxiety disorders or stress.

10. The method of claim 9, wherein the amount of the pharmaceutical composition administered is about 1 g/day to about 15 g/day.

11. The method of claim 9, wherein the administration of said composition causes an increase in the level of BDNF in the brain of the treated patient, and/or an increase in the level of cortisol in the blood of the treated patient.

* * * * *